United States Patent [19] [11] 4,010,649
Falk [45] Mar. 8, 1977

[54] MOLTEN METAL SAMPLERS WITH FLOW DIVERTER

[76] Inventor: Richard A. Falk, 519 Westminster Drive, Waukesha, Wis. 53186

[22] Filed: Nov. 10, 1975

[21] Appl. No.: 630,467

[52] U.S. Cl. .................. 73/425.4 R; 73/DIG. 9
[51] Int. Cl.² ................................ G01N 1/12
[58] Field of Search ............. 73/425.4 R, DIG. 9

[56] References Cited
UNITED STATES PATENTS 3,415,125 12/1968 Collins .................. 73/DIG. 9
3,877,309 4/1975 Hance .................... 73/DIG. 9

Primary Examiner—S. Clement Swisher
Attorney, Agent, or Firm—Henry C. Fuller

[57] ABSTRACT

A sampler for taking a sample of molten metal from any source of molten metal includes a mold having a mold cavity with a fill passage and a flow diverter located within the mold cavity which causes turbulent flow of the molten metal as it enters the mold cavity to provide good mixing of the deoxidant and eliminate structural voids in the sample. In one embodiment, a pin sample tube has its inner end located in the path of flow from the fill passage to cause disruption of the normal flow patterns and provide the desired uniform sample.

9 Claims, 8 Drawing Figures

U.S. Patent    Mar. 8, 1977    4,010,649
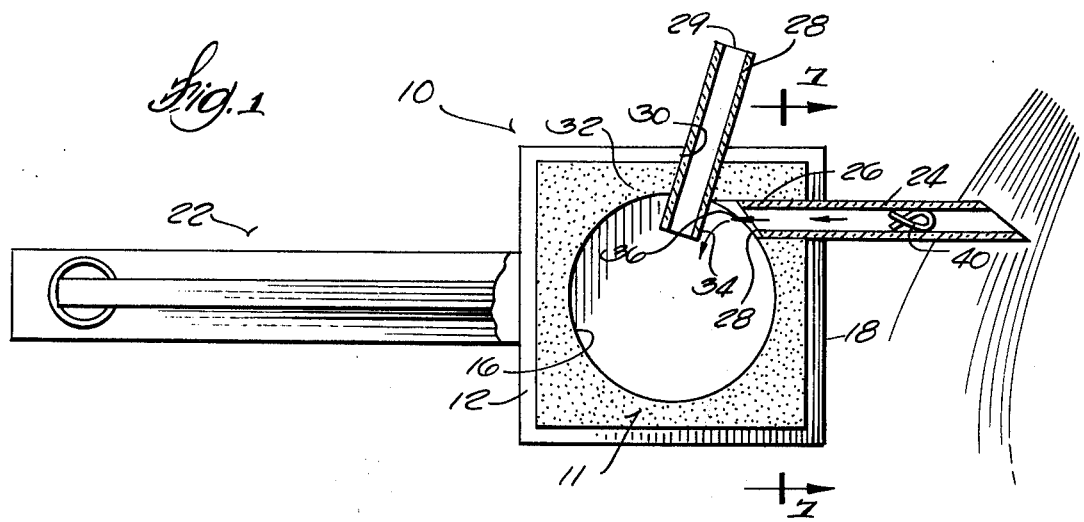
Fig. 1
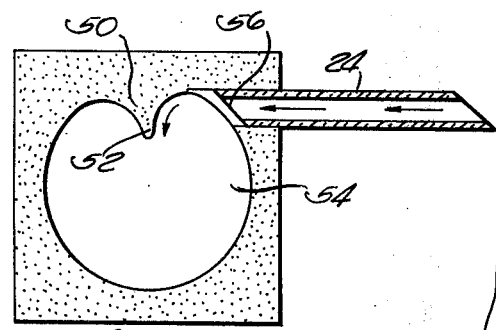
Fig. 2
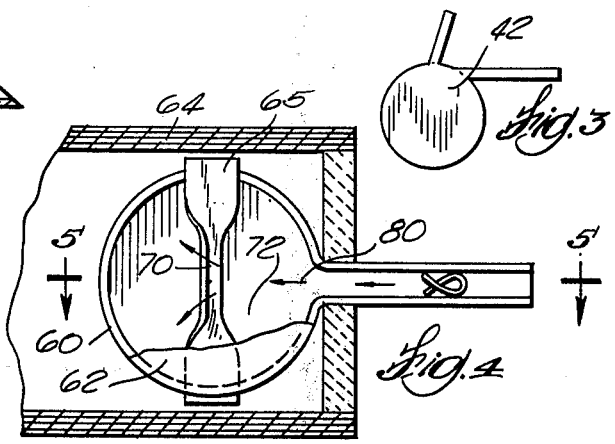
Fig. 3 / Fig. 4
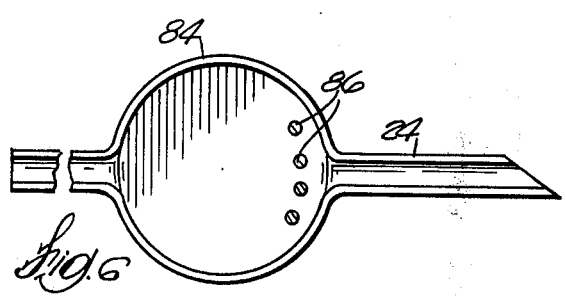
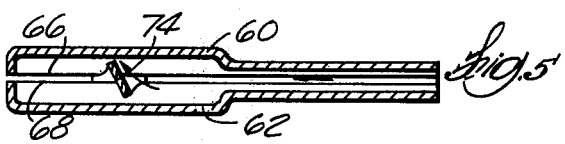
Fig. 5
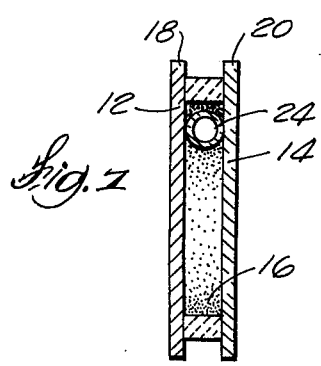
Fig. 6
Fig. 7
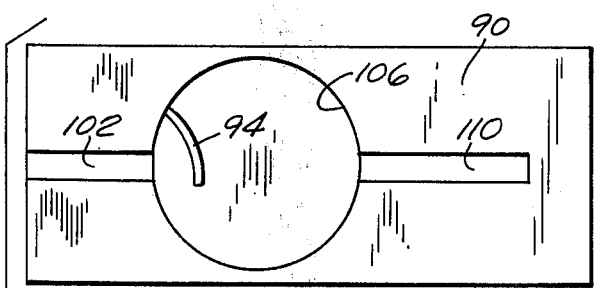
Fig. 8
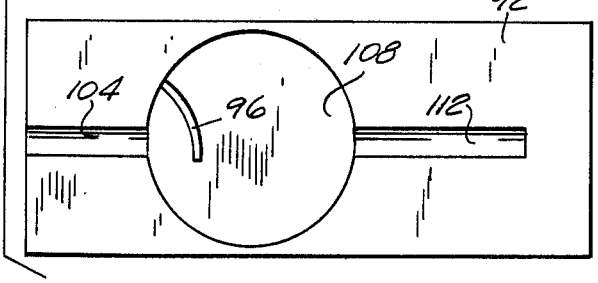

4,010,649

MOLTEN METAL SAMPLERS WITH FLOW DIVERTER

BACKGROUND OF THE INVENTION

It has become common in the art of molten metal sampling to simultaneously obtain both disc and pin samples with the disc suitable for spectographic analysis and the pin adapted for use in induction furnace combustion analysers. My patents U.S. Pat. Nos. 3,859,857 and 3,805,621 show mold structures adapted to provide both pin samples and disc samples. It has been known for some time that pin samples and disc samples taken simultaneously have differed in homogenity and the state of deoxidation and thus, the results from spectographic analysis and combustion analysis do not always correlate. Furthermore, structural voids caused by entrapped air have been detected in some disc samples obtained with prior art samplers. It is an object of the present invention to provide a more representative sample and eliminate structural voids and thus, overcome the deficiencies noted in the prior art sampling devices.

SUMMARY OF INVENTION

The invention provides a molten metal sampler in which diverter means are provided within the mold cavity and positioned relative to the mold fill passage to cause turbulent flow of metal entering the mold cavity to afford better mixing of the molten metal and the deoxidant and to eliminate entrapped air.

Various types of diverter means are disclosed herein which have provided good test results. In one embodiment, a pin sample tube has its inner end located within the mold cavity and in the molten metal flow path as the molten metal exits the fill passage to cause the desired turbulence and mixing. Thus, the fill tube serves a dual purpose and eliminates the need for any special structure for baffles or diverters to accomplish the intended results of this invention. In other embodiments the mold halves have integrally formed projections or wall means to cause flow diversion from the normal unobstructed flow in prior art samplers.

Further objects, advantages and features of the invention will become apparent from the following disclosure.

DESCRIPTION OF DRAWINGS

FIG. 1 is a sectional view of a stream sampler in accordance with the invention.

FIG. 2 shows a further embodiment of a stream sampler in accordance with the invention.

FIG. 3 shows in reduced scale a sample formed by the sampler shown in FIG. 1.

FIG. 4 is a sectional view of a sampler for pneumatic and immersion sampling.

FIG. 5 is a view along line 5—5 of FIG. 4.

FIG. 6 is a sectional view of an additional embodiment of a stream sampler.

FIG. 7 is a sectional view along line 7—7 of FIG. 1.

FIG. 8 is an elevational view of a further embodiment of the sampler of the invention.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

In the drawings, FIGS. 1 and 7 show a stream sampler 10 of the general configuration of the stream sampler shown in my pending application Ser. No. 590,528. The stream sampler 10 as shown, has a solid body 11 with an annular cavity 16, and opposed open faces 12 and 14. The faces are sealed by the jaws 18 and 20 of a clamp and mold holder 22 as illustrated in the aforesaid application. The stream sampler 10 is provided with an inlet passage in the form of a fused quartz fill tube 24 which extends through a slot or bore 26 in the mold body 11. A pin sample tube 28 with a bore or sample passage 29 extends through a slot or bore 30 in the wall portion 32 of the mold body 11.

In accordance with the invention, the pin sample tube 28 has an inner end 34 which is located in the linear fill path axis 36 of molten metal passing through the fill tube 24. By obstructing and disturbing flow, the end 34 of the stream sample tube causes turbulence and thorough mixing of the deoxidant 40 which can be contained in the fill tube 24 or in the mold cavity 16. FIG. 3 is a view in reduced scale of a sample 42 obtained with a sample mold of the type shown in FIG. 1. The member 28, of course, can be a solid rod rather than a fused quartz tube pin sample tube to obtain the advantages of the invention.

FIG. 2 shows a modified embodiment of a stream sampler in which the mold body 50 is provided with a projection 52 which extends inwardly toward the center of the mold cavity 54 and which is located in the flow path 56 from the fill tube 24.

FIG. 4 and 5 show a sampler suitable for immersion or pneumatic sampling from any source of molten metal and which includes two mold halves 60, 62 which are contained within a protective housing 64. The mold halves are separated by a spacer 65 which is located between the inner edges 66, 68 of the mold halves to provide an air vent. The spacer 65 includes a web portion 70 which spans the mold cavity 72. The spacer 65 has an angularly related portion 74 located centrally of the mold cavity and in the path 80 of the molten metal flow to cause the desired turbulence.

FIG. 6 shows a further embodiment of a sampler 84 in which the flow diverting means comprises an array of spaced pins 86 located opposite the fill tube 24. If the mold halves are formed from metal the pins 86 can be welded to one of the mold halves.

FIG. 8 shows two mold halves 90, 92 which can be cast from refractory or formed from metal for a chill mold with each mold half containing a diverter segment 94, 96 which together, when mold halves 90, 92 are assembled, provide a diverter which substantially spans the width of the mold cavity. In the FIG. 8 embodiment, the fill passage is defined by elongated semi-circular grooves 102, 104 which communicate with recesses 106, 108 which form the mold cavity. Grooves 110, 112 cooperate to define a pin sample mold.

I claim:

1. A molten metal sampler comprising wall means defining a mold cavity for forming a sample, wall means defining a sample entry passage having an inlet for receiving molten metal and an outlet communicating with said mold cavity and providing a linear flow path of metal into said cavity, flow diverter means on said wall means defining said mold cavity and located in said mold cavity and positioned in said mold cavity to divert the flow of molten metal within said mold cavity from said linear flow path to afford thorough mixing of the deoxidant and provide a uniform sample free of structural voids.

2. A molten metal sampler comprising wall means defining a mold cavity for forming a sample, wall means defining a sample entry passage having an inlet for receiving molten metal and an outlet communicating with said mold cavity and flow diverter means located in said mold cavity and positioned in said mold cavity to disturb the flow of molten metal into said mold cavity to afford thorough mixing of the deoxidant and provide a uniform sample, wherein said flow diverter means comprises a pin sample tube extending through the wall means defining said mold cavity and communicating with said mold cavity with said pin sample tube having an inner end located in the path of molten metal flow through said outlet of said sample entry passage.

3. A molten metal sampler in accordance with claim 2 wherein said sample entry passage provides a molten metal flow into said mold cavity along a linear axis and wherein said pin sample tube inner end intercepts said axis within said mold cavity.

4. A molten metal sampler in accordance with claim 2 wherein said wall means defining a mold cavity comprises a solid body having walls forming the periphery for an open-faced mold cavity and wherein said pin sample tube extends through a slot in the mold body.

5. A molten metal sampler in accordance with claim 1 wherein said flow diverter means comprises an integral projection extending from a mold body wall into the flow path of molten metal entering said mold cavity.

6. A molten metal sampler comprising wall means defining a mold cavity for forming a sample, wall means defining a sample entry passage having an inlet for receiving molten metal and an outlet communicating with said mold cavity and flow diverter means located in said mold cavity and positioned in said mold cavity to disturb the flow of molten metal into said mold cavity to afford thorough mixing of the deoxidant and provide a uniform sample wherein said wall means defining a mold cavity comprises two opposed mold halves and wherein said flow diverter means comprises a spacer having first portions located between and separating said mold halves to provide an air vent and spanning said mold cavity with said spacer having a second portion located in the flow path from said entry port and inclined at an angle with respect to said first portions to engage and divert metal flowing through said fill passage into said mold cavity.

7. A molten metal sampler comprising wall means defining a mold cavity for forming a sample, wall means defining a sample entry passage having an inlet for receiving molten metal and an outlet communicating with said mold cavity and flow diverter means located in said mold cavity and positioned in said mold cavity to disturb the flow of molten metal into said mold cavity to afford thorough mixing of the deoxidant and provide a uniform sample, wherein said wall means defining a mold cavity comprises two mold halves formed from metal and wherein said flow diverter means comprises an array of spaced pegs fixed to said mold halves with said array of pegs arranged about the mold cavity to intercept metal flow into said cavity.

8. A molten metal sampler comprising wall means defining a mold cavity for forming a sample, wall means defining a sample entry passage having an inlet for receiving molten metal and an outlet communicating with said mold cavity and flow diverter means located in said mold cavity and positioned in said mold cavity to disturb the flow of molten metal into said mold cavity to afford thorough mixing of the deoxidant and provide a uniform sample wherein said wall means defining a mold cavity comprises two opposed mold halves and wherein said flow diverter means comprises wall portions on each of said mold halves which cooperate with each other when assembled to provide a single diverter, said diverter being located in the linear flow path of metal entering said cavity.

9. A molten metal sampler comprising wall means defining a sample mold cavity, wall means defining a tubular sample fill passage communicating with said mold cavity and providing a uniform linear flow path of metal into said cavity, a deoxidant located in one of said fill passages and said sample cavity and means in said sample cavity connected to said sample mold wall means and positioned in the flow path of metal into said cavity from said fill passage to divert metal flow entering said cavity from said linear flow path to enhance mixing of said deoxidant with molten metal in said cavity and eliminate structural voids in the sample.

* * * * *